United States Patent
Foley et al.

(10) Patent No.: US 10,934,239 B2
(45) Date of Patent: *Mar. 2, 2021

(54) FILM OZONOLYSIS IN A TUBULAR OR MULTITUBULAR REACTOR

(71) Applicant: P2 Science, Inc., Woodbridge, CT (US)

(72) Inventors: Patrick Foley, New Haven, CT (US); Neil Burns, Freehold, NJ (US); Alexandre Chapeaux, New Haven, CT (US); Icilio Adami, Milan (IT); Antonio Milicia, Milan (IT)

(73) Assignee: P2 Science, Inc., Woodbridge, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/541,065

(22) Filed: Aug. 14, 2019

(65) Prior Publication Data

US 2020/0039910 A1 Feb. 6, 2020

Related U.S. Application Data

(63) Continuation of application No. 16/057,235, filed on Aug. 7, 2018, now Pat. No. 10,428,001, which is a continuation of application No. 15/320,250, filed as application No. PCT/US2015/036589 on Jun. 19, 2015, now Pat. No. 10,071,944.

(60) Provisional application No. 62/163,022, filed on May 18, 2015, provisional application No. 62/015,311, filed on Jun. 20, 2014.

(51) Int. Cl.
| | |
|---|---|
| *C07C 45/40* | (2006.01) |
| *B01J 10/00* | (2006.01) |
| *B01J 19/00* | (2006.01) |
| *B01J 19/24* | (2006.01) |
| *C07C 51/34* | (2006.01) |
| *B01J 10/02* | (2006.01) |
| *C02F 1/78* | (2006.01) |
| *C02F 101/30* | (2006.01) |

(52) U.S. Cl.
CPC .............. *C07C 45/40* (2013.01); *B01J 10/02* (2013.01); *B01J 19/247* (2013.01); *B01J 19/2415* (2013.01); *B01J 19/2425* (2013.01); *C02F 1/78* (2013.01); *C07C 51/34* (2013.01); *B01J 2219/24* (2013.01); *C02F 2101/30* (2013.01); *C02F 2201/784* (2013.01); *C07C 2601/16* (2017.05)

(58) Field of Classification Search
CPC ....... C07C 45/40; B01J 10/02; B01J 19/2415; B01J 19/247
See application file for complete search history.

(56) References Cited

U.S. PATENT DOCUMENTS

| | | |
|---|---|---|
| 2,813,113 A | 11/1957 | Goebel et al. |
| 3,023,244 A | 2/1962 | Eschinasi |
| 3,699,169 A | 10/1972 | Bertele et al. |
| 4,296,258 A | 10/1981 | Fehr et al. |
| 4,311,617 A | 1/1982 | Ansari et al. |
| 4,491,537 A | 1/1985 | Futoshi et al. |
| 4,791,228 A | 12/1988 | Siclari et al. |
| 4,940,808 A | 7/1990 | Schulz et al. |
| 5,292,941 A | 3/1994 | Kigawa et al. |
| 5,543,565 A | 8/1996 | McVay et al. |
| 5,756,821 A | 5/1998 | Dilk et al. |
| 5,801,275 A | 9/1998 | McVay et al. |
| 6,309,521 B1 | 10/2001 | Andrews et al. |
| 6,395,695 B1 | 5/2002 | Sivik |
| 6,512,131 B1 | 1/2003 | Best et al. |
| 6,545,186 B2 | 4/2003 | Giselbrecht et al. |
| 6,548,715 B1 | 4/2003 | Bouillion et al. |
| 7,825,277 B2 | 11/2010 | Gutsche et al. |
| 7,968,742 B2 | 6/2011 | Aigner et al. |
| 8,221,708 B2 | 7/2012 | Seebauer et al. |
| 9,035,091 B2 | 5/2015 | Foley et al. |
| 9,604,898 B2 | 3/2017 | Foley et al. |
| 9,682,914 B2 | 6/2017 | Foley et al. |
| 9,701,606 B2 | 7/2017 | Goeke et al. |
| 9,840,449 B2 | 12/2017 | Foley et al. |
| 10,011,582 B2 | 7/2018 | Foley et al. |
| 10,071,944 B2 | 9/2018 | Foley et al. |
| 10,280,131 B2 | 5/2019 | Foley et al. |
| 2003/0078453 A1 | 4/2003 | Springer et al. |
| 2003/0100781 A1 | 5/2003 | Springer et al. |
| 2004/0186042 A1 | 9/2004 | Schmaus et al. |
| 2007/0010688 A1 | 1/2007 | Ko et al. |
| 2007/0142666 A1 | 6/2007 | Himeno et al. |
| 2007/0276165 A1 | 11/2007 | Gutsche et al. |
| 2009/0221083 A1 | 9/2009 | White et al. |
| 2010/0152479 A1 | 6/2010 | Seebauer et al. |
| 2013/0078685 A1 | 3/2013 | Ulrich et al. |
| 2013/0177497 A1 | 7/2013 | Fitch et al. |
| 2013/0338150 A1 | 12/2013 | Boehme et al. |

(Continued)

FOREIGN PATENT DOCUMENTS

| | | |
|---|---|---|
| CA | 1144561 | 4/1983 |
| CA | 2247662 A1 | 3/1999 |

(Continued)

OTHER PUBLICATIONS

English Abstract of Japanese Publication No. H06-135878, published May 17, 1994.

(Continued)

*Primary Examiner* — Sikarl A Witherspoon
(74) *Attorney, Agent, or Firm* — Hoxie & Associates LLC (57) ABSTRACT

The disclosure relates to a method of performing ozonolysis or ozone-based oxidation on a liquid or emulsified reagent using a tubular falling firm reactor with one or multiple tubes wherein the combined ozone and carrier gas flow is co-current.

23 Claims, 1 Drawing Sheet

(56) References Cited

U.S. PATENT DOCUMENTS

| | | |
|---|---|---|
| 2014/0316149 A1 | 10/2014 | Wickens et al. |
| 2014/0357547 A1 | 12/2014 | Goeke et al. |
| 2015/0183707 A1 | 7/2015 | Foley et al. |
| 2017/0247314 A1 | 8/2017 | Foley et al. |
| 2017/0275230 A1 | 9/2017 | Foley et al. |

FOREIGN PATENT DOCUMENTS

| | | |
|---|---|---|
| CN | 102653531 A | 9/2012 |
| CN | 102795987 A | 11/2012 |
| EP | 0555472 A1 | 8/1993 |
| EP | 0761629 A1 | 3/1997 |
| EP | 1860093 A1 | 11/2007 |
| GB | 2043067 A | 10/1980 |
| JP | H06-135878 | 5/1994 |
| WO | WO 1993/002991 | 2/1993 |
| WO | WO 1995/001960 | 1/1995 |
| WO | WO 2002/048431 | 6/2002 |
| WO | WO 2007/068498 | 6/2007 |
| WO | WO 2009/061806 | 5/2009 |
| WO | WO 2012/177357 | 12/2012 |
| WO | WO 2013/053102 | 4/2013 |
| WO | WO 2015/039010 | 3/2015 |
| WO | WO 2015/106293 | 7/2015 |
| WO | WO 2015/126936 | 8/2015 |
| WO | WO 2015/191706 | 12/2015 |
| WO | WO 2015/196019 | 12/2015 |
| WO | WO 2016/091895 | 6/2016 |
| WO | WO 2017/223220 | 12/2017 |
| WO | WO 2018/053289 | 3/2018 |

OTHER PUBLICATIONS

Abe, et al, "Synthesis of Massoia lactone and its analogs. I. Synthesis of the lactone of 1-decen-4-ol-1-carboxylic acid," 75 Nippon Kagaka Kaishi, Pure Chem., 953-5, (1921-1947), (1954). [CAS Abstract Only].
Avdeev, et al., "Molecular Mechanism of Oxygen Isotopic Exchange over Supported Vanadium Oxide Catalyst Vox/TiO2," *The Journal of Physical Chemistry C*, vol. 117, No. 6, pp. 2879-2887, (2013).
Ayer, et al., "Degraded Monoterpenes from the Opisthobranch Mollusc *Melibe leonina*," *Short Communications*, Experientia 39, Birkhauser Verlag, CH-4010 Basel/Switzerland, (1983), 2 pages.
Cermak, et al., "Synthesis of δ-Stearolactone from Oleic Acid," *JAOCS*, vol. 77, No. 3, pp. 243-248, (2000).
Chen, et al., "A Predictably Selective Aliphatic C—H Oxidation Reaction for Complex Molecule Synthesis," *Science*, vol. 318, (2007).
Chmielewski, et al., "Organic Syntheses Under High Pressure. 3. General Approach to the Synthesis of Naturally Occuring .delta.-lactones," *The Journal of Organic Chemistry*, vol. 46, No. 11, pp. 2230-2233, (1981).
"Aliphatic Carboxylic Acids," Competition Science Vision Aug. 2000, *Pratiyogita Darpan*, vol. 3, No. 30, pp. 799. [ 2 pages].
Cook, et al., "Study of the Total Synthesis of (-)-Exiguolide," *J. Org. Chem.*, vol. 77, pp. 6728-6742, (2012).
Cullen, William, "Re: Melibe from Alaska," Jan. 12, 2001, Australian Museum, Sydney, pp. 1-4.
Dupe, et al., "Methyl Ricinoleate as Platform Chemical for Simultaneous Production of Fine Chemicals and Polymer Precursors," *ChemSusChem.*, vol. 5, pp. 2249-2254, (2012).
Förtsch, et al., "Synthese, Kristallstruktur und Reaktionen neuartiger metallacyclischer Dioxo- und Aminooxocarben-Komplexe des Eisens," *Chem. Ber.*, vol. 127, pp. 711-715, (1994). [English Abstract Only.].
Gerth, et al., "Synthesis of δ-Lactones via Radical C—C Bond Formation Using Chiral Radical Precursors," *J. Org. Chem.*, vol. 51, pp. 3726-3729, (1986).
Gross, R.A., Jr., "Ozonolysis Problems That Promote Student Reasoning," *Journal of Chemical Education*, vol. 83, No. 4, pp. 604-609, (2006).

Harding, et al., "beta-Methyl-delta-dodecadiene and beta-Methyl-delta-decadiene," *Journal of the Chemical Society*, Transactions, pp. 448-451, (1911).
Hearn, et al., "Kinetics and Product Studies for Ozonolysis Reactions of Organic Particles Using Aerosol CIMS," *The Journal of Physical Chemistry A*, vol. 108, No. 45, pp. 10019-10029, (2004).
Kadesch, R.G., "Ozonolysis of Fatty Acids and Their Derivatives," *Progress in the Chemistry of Fats and Other Lipids*, vol. 6, pp. 291-312, (1963).
Kauffmann, et al., "Ubergangsmetallaktivierte organische Verbindungen, XXXVIII. Chemoselektive nucleophile Methylierungen durch In-Situ-Blockierung von Aldehydgruppen unter [alpha]1-Phosphonioalkoxid-Bildung," *Chemishe Berichte*, pp. 459-464, (1993). [No English Translation.].
Kula, et al., "Synthesis of Enantiomerically Pure Volatile Compounds Derived From (R)-3-Hydroxynonanal," *Tetrahedron: Asymmetry*, vol. 11, pp. 943-950, (2000).
Lee, et al., "Tin-free, Radical-mediated Gamma-alkylations of Alpha, Beta-unsaturated Esters via O-tert-alkyl Dienol Ethers," vol. 1, pp. 49-54, (2008).
Maggiolo, A. "Ozonization of Fatty Acids and Their Derivatives," *The Journal of the American Oil Chemists' Society*, vol. 40, pp. 161-164, (1963).
Otsubo, et al., "A Direct Synthesis of [gamma]-, [delta], and [epsilon]-Lactones Utilizing SmI2-induced Barbier-type Reaction in the Presence of Hexamethylphosphoric Triamide (HMPA)," *Chemistry Letters*, pp. 1487-1490, (1987). Http://www.journal.csj.jp/doi/pdf/10.1246/c1.1987.1487 [retrieved on May 29, 2017].
PubChem-CID-107500001, Oct. 26, 2006, 17 pages.
Quan, et al., "A Convenient Protecting Group for Aldehydes," *Synlett*, vol. 2001, No. 12, pp. 1925-1926, (2001).
Rani, et al., "Ozonolysis of Oleic Acid Over a Nano Vanadium Pentoxide (V2O5) Catalyst," *European Journal of Scientific Research*, vol. 24, No. 3, pp. 428-432, (2008).
Richardson, et al., "A Practical Synthesis of Long-Chain Iso-Fatty Acids (iso-C12-C19) and Related Natural Products," *Beilstein Journal of Organic Chemistry*, vol. 9, pp. 1807-1812, (2013).
Rosenberger, et al., "28. Synthesis of δ-Lactones From Glutaraldehyde," *Helvetica Chimica Acta*, vol. 55, pp. 249-255, (1972).
Sabitha, et al., "The First Asymmetic Total Synthesis of (R)-Tuberolactone, (S)-Jasmine Lactone, and (R)-δ-Decalactone," *Tetrahedron Letters*, vol. 47, pp. 8179-8181, (2006).
Schiaffo, C.E., "I. An Improved Procedure for Alkene Ozonolysis. II. Expoloring a New Structural Paradigm for Peroxide Antimalarials," *Student Research Projects, Dissertations, and Theses—Chemistry, Department, University of Nebraska-Lincoln*, (Jun. 2011), Paper 23.
Shao, et al., "Asymmetric Hydrogenation of 3,5-Dioxoesters Catalyzed by Ru-binap Complex: A Short Step Asymmetric Synthesis of 6-Substituted 5,6-dihyrdo-2-pyrones," *Tetrahedron*, vol. 49, No. 10, pp. 1997-2010, (1993).
Shekhter, et al., "Study of Compounds with Juvenile-hormone Activity. X. Synthesis of Esters of 2E,4E-3,11-dimethyl-11-methoxy-2,4-dodecadienic and 2E,4E-2, 11-dimethyl-2,4,10-dodecatrienic acids," *Zhurnal Organicheskoi Khimii*, vol. 15, No. 2, pp. 260-264, (1979).
Shono, et al., "Electroreductive Intermolecular Coupling of Ketones with Olefins," *J. Org. Chem.*, vol. 54, No. 26, pp. 6001-6003, (1989).
STN 1984 (Year: 1984), p. 1.
STN Nov. 1984 (Year: 1984), 1 Page.
STN 1995 (Year: 1995), 1 Page.
STN Sep. 29, 2005 (Year: 2005), 1 Page.
STN Mar. 7, 2013 (Year: 2013), 1 Page.
Surburg, et al., *Common Fragrance and Flavor Materials*, 5th Ed. Wiley-VCH, pp. 149-172, (2006).
Tanaka, et al., "Syntheses of (5E)-PGE2 and New 6-Functionalized Derivatives by the Use of Palladium-Catalyzed Decarboxylative Allylic Alkylation," *Tetrahedron*, vol. 42, No. 24, pp. 6747-6758, (1986).
Utaka, et al., "New Synthesis of Jasmine Lactone and Related-δ-Lactones from 1,2 Cyclohexanedione. Preparation and Dye- (56) References Cited

OTHER PUBLICATIONS

Sensitized Photooxygenation of 3-(2-Alkenyl)- and 3-(2-Alkynyl)-1,2-cyclohexanediones," *J. Org. Chem.*, vol. 51, No. 6, pp. 935-938, (1986).

Wasmi, et al, "Synthesis of Vanadium Pentoxide Nanoparticles as Catalysts for the Ozonation of Palm Oil," *Ozone: Science & Engineering*, vol. 38, No. 1, pp. 36-41, (2015).

Willand-Charnley, et al., "Pyridine is an Organocatalyst for the Reactive Ozonolysis of Alkenes," *Org. Lett.*, vol. 14, No. 9, pp. 2242-2245, (2012).

Written Opinion of the International Searching Authority for International Application No. PCT/US2017/051817 dated Dec. 8, 2017, 9 pages.

Yahata, et al., "Methodology for in Situ Protection of Aldehydes and Ketones Using Trimethylsilyl Trifluoromethanesulfonate and Phosphines: Selective Alkylation and Reduction of Ketones, Esters, Amides, and Nitriles," *Chem. Pharm. Bull.*, vol. 61, No. 12, pp. 1298-1307.

Cornforth, et al., "Studies of Cholesterol Biosynthesis 1. A New Chemical Degradation of Cholesterol," *Biochemical Journal*, vol. 54, pp. 590-597, (1953).

Mori, et al., "Synthesis of mono- and sesquiterpenoids—I: Racemic norcaran-2-one, trans-caran-2-one and trans-dihydrosesquicaran-2-one," *Tetrahedron*, vol. 25, No. 20, pp. 5013-5018, (1969); Abstract Only.

Mori, et al., "Synthesis and biological activity of both (E)- and (Z)-isomers of optically pure (S)-14-methyl-8-hexadecenal (trogodermal), the antipodes of the pheromone of the khapra beetle," *Tetrahedron*, vol. 38, No. 15, pp. 2291-2297, (1982); Abstract Only.

Omonov, et al., "The Production of Biobased Nonanal by Ozonolysis of Fatty Acids," *RSC Adv.*, vol. 4, pp. 53617-53627, (2014); DOI: 10.1039/c4ra07917e.

Petit, et al., "Stereoselective Synthesis of Optically Active α-methyl Esters," *Tetrahedron Letters*, vol. 31, No. 15, pp. 2149-2152, (1990); Abstract Only.

Burckhardt, H., et al., "Oxy-aldehyde (VII.)," *Berichte Der Deutschen Chemischen Gesellschaft Abteilung B:Abhandlungen*, vol. 57, No. 10, pp. 1911-1917, (1924); Retrieved from the Internet: https://api.wiley.com/onlinelibrary/tdm/v1/articles/10.1002%2Fcber.19240571024 [retrieved on Jan. 23, 2006]; No English Translation Available.

Chudasama, V., et al, "Metal-free, Hydroacylation of C=C and N=N bonds via Aerobic C—H Activation of Aldehydes, and Reaction of the Products Thereof," *Org. Biomol. Chem.*, vol. 11, pp. 7301-7317, (2013).

Li, X., et al, "The Conversion of 5-hydroxymethyl Furfural (HMF) to Maleic Anhydride with Vanadium-based Heterogeneous Catalysts," *Green Chem.*, vol. 18, pp. 643-647, (2016).

FILM OZONOLYSIS IN A TUBULAR OR MULTITUBULAR REACTOR

CROSS-REFERENCE TO RELATED APPLICATIONS

This application is a continuation of U.S. application Ser. No. 16/057,235, filed on Aug. 7, 2018, which is a continuation of U.S. application Ser. No. 15/320,250, filed on Dec. 19, 2016, which is a National Stage Entry under 35 U.S.C. § 371 of International Application No. PCT/US15/36589, filed Jun. 19, 2015, which claims priority to U.S. Provisional Application No. 62/015,311, filed Jun. 20, 2014, and U.S. Provisional Application No. 62/163,022, filed May 18, 2015, each of which are incorporated herein by reference in their entireties.

BACKGROUND

Ozonolysis or ozone-based oxidation of reagents currently in use in the chemical industry generally rely on processing large amounts of material in either tray-type continuous ozonation systems or in batch systems, e.g., U.S. Pat. No. 2,813,113. The use of either type of established method, however, results in the accumulation of peroxide intermediates that can be unstable and present a significant explosion risk. Alternatively, processing small amounts of material in a continuous fashion can significantly reduce these risks. Solutions to address this important safety issue include the use of microstructured falling film reactors such as those described in U.S. Pat. No. 7,825,277 B2, and available from ThalesNano, Inc. These technologies, however, have not been adapted for use in large-scale (multi-ton) manufacturing processes, owing to challenges with throughput and the operation costs associated with maintaining large numbers of reaction vessel channels and precisely calibrated instruments.

Other commercial reaction technologies use sparging or aeration techniques to drive interactions between liquid and gaseous reagents, which can introduce local hot spots and requires that the gaseous reagent be present at high pressures. The disclosure described herein addresses the need for a method of industrial-scale ozonolysis that is safer and more efficient than conventional methods.

SUMMARY OF THE DISCLOSURE

The approach to ozonolysis described herein functions using gravity assisted co-current reagent flow to facilitate gaseous reagent diffusion into a liquid or emulsified reagent, which simplifies the reaction setup and minimizes the mechanical energy required, all while achieving a scalable and continuous process that does not allow for the accumulation of large amounts of hazardous intermediates, thus rendering the process and equipment described herein suitable for large, industrial-scale ozonolysis.

In one embodiment of the current disclosure a monotubular or multitubular reactor is used for ozonolysis or ozone-based oxidation in which:
  (a) homogeneity of the reagent-containing film and thermal exchange is maximized,
  (b) selection of the optimum size of the individual tubes is based on the best compromise between maximum internal diameter (for optimum throughput) and minimum height (for reduced head loss) while maintaining mechanical simplicity (for reduced maintenance), and
  (c) distribution of the gaseous ozone-containing reagent with negligible head loss is conditioned by the reagent-containing film thickness and corresponding flow rate such that the conversion and temperature profiles are optimized along the tube length.

The parameters above can be optimized both theoretically and empirically, and can be used to ensure excellent results without the need for calibration when changing the flow rate and/or composition of the liquid or emulsified reagent.

In some embodiments, the method of performing ozonolysis or ozone-based oxidation on a liquid or emulsified reagent entails using a tubular falling film reactor with one or multiple tubes wherein the combined ozone and carrier gas flow is co-current.

In some embodiments, the diameter of the tube(s) is between 5 mm and 5 m.

In some embodiments, the diameter of the tube(s) is between 5 mm and 50 mm.

In some embodiments, the diameter of the tube(s) is between 5 mm and 30 mm.

In some embodiments, the diameter of the tube(s) is between 10 mm and 25 mm.

In some embodiments, the diameter of the tube(s) is 25 mm.

In some embodiments, the diameter of the tube(s) is 10 mm.

In some embodiments, the diameter of the tube is between 50 mm and 5 m.

In some embodiments, the diameter of the tube is between 0.5 m and 5 m.

In some embodiments, the diameter of the tube is between 50 mm and 5 m and an annular element is added to the center of the tube to regulate gas flow and to add additional film surface area.

In some embodiments, the length of the tube(s) is between 1 and 20 m.

In some embodiments, the length of the tube(s) is between 1 and 7 m.

In some embodiments, the length of the tube(s) is 1.7 m.

In some embodiments, the length of the tube(s) is 6 m.

In some embodiments, the length of the tube(s) is between 7 and 20 m.

In some embodiments, the distribution of gas within the tube(s) may be controlled by annular spaces for gas flow within the tube(s).

In some embodiments, multiple falling film tube reactors are used in series to process a continuous stream of liquid or emulsified reagent.

In some embodiments, the method of performing ozonolysis or ozone-based oxidation on a liquid or emulsified reagent with a gaseous reagent (e.g., comprising ozone and one or more carrier gases) includes:
  (a) feeding the liquid or emulsified reagent from a common liquid or emulsified reagent feeding chamber that is maintained completely full through annular slots and into a plurality of parallel and substantially identical tubes, as to form a liquid or emulsified reagent film on the internal surface of each tube;
  (b) feeding the gaseous reagent through the annular slots and into the tubes from a gaseous reagent feeding chamber, the feeding pressure of the gaseous reagent being substantially the same as the pressure loss from the gaseous reagent flow through the tubes containing the liquid or emulsified reagent film, but less than the feeding pressure of the liquid reagent;
  (c) cooling the tubes by flowing a liquid coolant through a housing surrounding the tubes; and (d) collecting reaction product(s) and gaseous reagent exhaust in one or more product containers connected to the end of the tubes opposite that connected to the annular slots.

In some embodiments, the length of the tubes used in this method is between 1 and 20 m.

In some embodiments, the length of the tubes used in this method is between 1 and 7 m.

In some embodiments, the length of the tubes used in this method is 1.7 m.

In some embodiments, the length of the tubes used in this method is 6 m.

In some embodiments, the length of the tubes used in this method is between 7 and 20 m.

In some embodiments, the internal diameter of the tubes used in this method is between 5 mm and 5 m.

In some embodiments, the internal diameter of the tubes used in this method is between 5 mm and 50 mm.

In some embodiments, the internal diameter of the tubes used in this method is between 5 mm and 30 mm.

In some embodiments, the internal diameter of the tubes used in this method is between 10 mm and 25 mm.

In some embodiments, the internal diameter of the tubes used in this method is 25 mm.

In some embodiments, the internal diameter of the tubes used in this method is 10 mm.

In some embodiments, the internal diameter of the tubes used in this method is between 50 mm and 5 m.

In some embodiments, the internal diameter of the tubes used in this method is between 0.5 m and 5 m.

In some embodiments, the feeding pressure of the gaseous reagent used in this method is between 0.1 and 5 bar.

In some embodiments, the feeding pressure of the gaseous reagent used in this method is between 0.1 and 0.5 bar.

In some embodiments, the feeding pressure of the gaseous reagent used in this method is between 0.2 and 0.4 bar.

In some embodiments, the feeding overpressure of the liquid or emulsified reagent with respect to the feeding pressure of the gaseous reagent is between 5 and 15 cm of liquid column.

In some embodiments, the carrier gas contains, at least in part, gaseous reagent exhaust from one or more product containers.

In some embodiments, the reagent is a liquid.

In some embodiments, the reagent is an emulsion in water.

In some embodiments, the liquid or emulsified reagent or reagent mixture is the starting material which is reacted with ozone to yield oxidized product(s).

In some embodiments, the starting material is an alkene, alkyne, or any other compound that may be oxidized with ozone.

In some embodiments, the liquid or emulsified reagent comprises hydroxycitronellene, methoxycitronellene, rose ketones (e.g., Ionone), fatty acid methyl esters (FAME), triglycerides, fatty acids, fatty alcohols, fatty esters, diterpenes, sesquiterpenes, monoterpenes, allyl ethers, alpha olefins, rosin acids, tertiary amines, alkanes, amides, carboxylic acids, or compounds containing an aromatic ring.

In some embodiments, the reagent introduced into the reactor is any compound that is susceptible to ozone oxidation. In some embodiments, the reagent comprises any alkane, amide, carboxylic acid, or aromatic ring.

In some embodiments, the reaction products may be further reduced or oxidized to generate corresponding carbonyls, alcohols, and/or acids.

In some embodiments, the liquid or emulsified reagent comprises hydroxycitronellene.

In some embodiments, the liquid or emulsified reagent is a hydroxycitronellene emulsion in water.

In some embodiments, the liquid or emulsified reagent is a hydroxycitronellene solution in methanol.

In some embodiments, the product of the method described herein is hydroxymelonal.

In some embodiments, the liquid or emulsified reagent comprises methoxycitronellene.

In some embodiments, the liquid or emulsified reagent is a methoxycitronellene emulsion in water.

In some embodiments, the liquid or emulsified reagent is a methoxycitronellene solution in methanol.

In some embodiments, the product is methoxymelonal.

In some embodiments, the liquid or emulsified reagent comprises fatty acid methyl esters (FAME).

In some embodiments, the liquid or emulsified reagent is a FAME emulsion in water.

In some embodiments, the liquid or emulsified reagent is a FAME solution in methanol.

In some embodiments, the product produced by the method described herein comprises methyl azealdehyde and nonanal.

In some embodiments, the liquid or emulsified reagent comprises an unsaturated olechemical such as a triglyceride, a fatty acid, a fatty alcohol, or a fatty acid ester.

In some embodiments, the liquid or emulsified reagent comprises a diterpene such as abietic acid or its ester.

In some embodiments, the liquid or emulsified reagent comprises a mono- or di-unsaturated sesquiterpene.

In some embodiments, the liquid or emulsified reagent comprises a mono- or di-unsaturated monoterpene or terpene derivative such as pinene or limonene.

In some embodiments, the liquid or emulsified reagent comprises an allyl ether of 10 to 30 carbon atoms.

In some embodiments, the liquid or emulsified reagent comprises an alpha olefin of 10 to 30 carbon atoms.

In some embodiments, the liquid or emulsified reagent comprises a rose ketone. In some embodiments the rose ketone is Ionone.

In some embodiments, the product of the method described herein is cyclocitral.

In some embodiments, the liquid or emulsified reagent comprises a tertiary amine.

In some embodiments, the product of the method described herein is an N-oxide derivative.

In some embodiments, the carrier gas is $O_2$.

In some embodiments, the carrier gas is a mixture of $O_2$ and $N_2$. In some embodiments, the carrier gas is about 95% $O_2$ and 5% about $N_2$, about 90% $O_2$ and about 10% $N_2$, about 85% $O_2$ and about 15% $N_2$, about 80% $O_2$ and about 20% $N_2$, about 70% $O_2$ and about 30% $N_2$, about 60% $O_2$ and about 40% $N_2$, about 50% $O_2$ and about 50% $N_2$, about 40% $O_2$ and about 60% $N_2$, about 30% $O_2$ and about 70% $N_2$, about 20% $O_2$ and 80% $N_2$, or 10% $O_2$ and 90% $N_2$, wherein the term "about" refers to the indicated percentage +/−2.5%.

In some embodiments, the carrier gas is about 95% $O_2$ and about 5% $N_2$.

In some embodiments, the carrier gas is air.

In some embodiments, the liquid or emulsified reagent comprises an alkene.

In some embodiments, the liquid or emulsified reagent comprises an alkyne.

In some embodiments, the primary component of the liquid or emulsified reagent is methyl oleate.

In some embodiments, the liquid or emulsified reagent is derived from soy.

In some embodiments, the liquid or emulsified reagent is derived from palm oils.

In some embodiments, the liquid or emulsified reagent is derived from algal oils.

In some embodiments, waste water can be the reagent introduced into the reactor for the purpose of treating the water.

DETAILED DESCRIPTION OF THE DISCLOSURE

The disclosure relates to the ozonolysis or ozone-related reactions which occur on the free surface of a film of a liquid or emulsified reagent or reagent mixture that is subject to the controlled amount of a gaseous reagent comprising ozone ($O_3$). The liquid or emulsified reagent or reagent mixture is the starting material which is reacted with ozone to yield oxidized product(s). The starting material is generally an alkene, alkyne, or any other compound that may be oxidized with ozone. The reaction products may be further reduced or oxidized to generate corresponding carbonyls, alcohols, and/or acids.

Performing ozone-based oxidation reactions in industrial-scale tubular falling film reactors (e.g., those originally designed for other processes, such as sulfonation) is advantageous for a variety of reasons. For example, tubular falling film sulfonation reactors operate by exposing relatively small volumes of liquid reagent(s) to relatively high volumes of reactive gaseous reagent(s) that have been diluted with an inert carrier gas or mixture thereof. Due to their continuous mode of operation, the reactors are efficient and exhibit reasonably high throughput rates per reactor tube, but do not allow for the accumulation of intermediates. Moreover, these reactors handle exothermic processes well because they include excellent heat dissipation features. The method described herein provides a safe and efficient means of performing ozonolysis reactions on an industrial scale by taking advantage of the aforementioned benefits of tubular falling film sulfonation reactors.

Examples of tubular falling film sulfonation reactors are described in GB 2,043,067 B, which is incorporated herein by reference. Tubular or multitubular co-current reactors are particularly useful due to their relatively low cost and mechanical simplicity. Such reactors can be adapted to use for ozonation reactions.

An additional safety advantage can be realized over traditional ozonolysis approaches if the reaction is carried out in water or as an emulsion with water. The flashpoint of the liquid reagent(s) can be eliminated or dramatically reduced in the presence of water, thereby minimizing the risk of fire in the event of an uncontrolled exotherm or explosion. Furthermore, the use of an emulsion allows for easier control of the liquid reagent in terms of concentration, distribution within the ozonolysis device tubes, and temperature.

Figure 1:
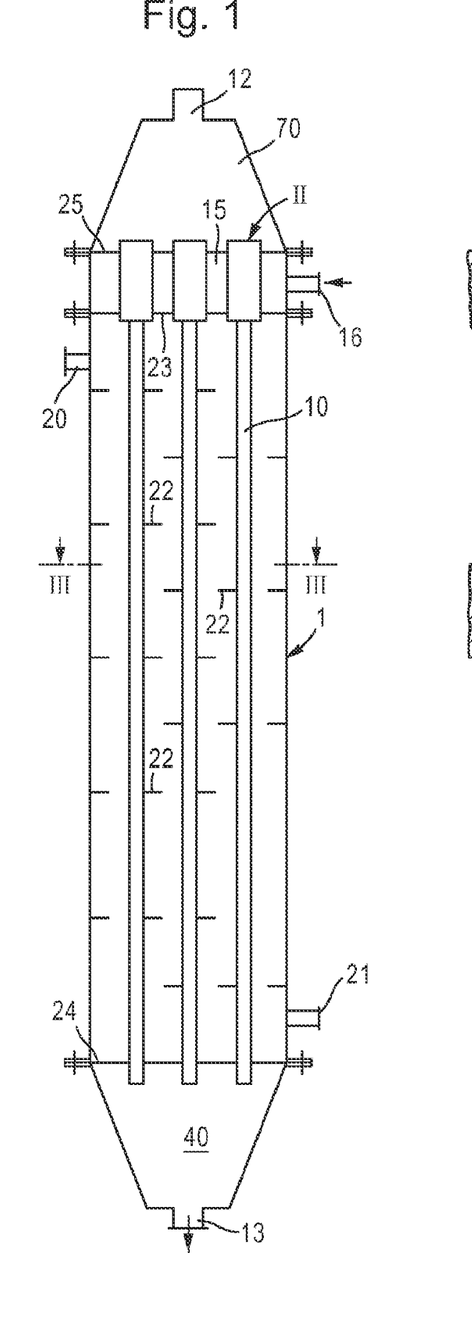
FIG. 1 is a diagram of the vertical cross-section of a multitubular reactor.
Figure 2:
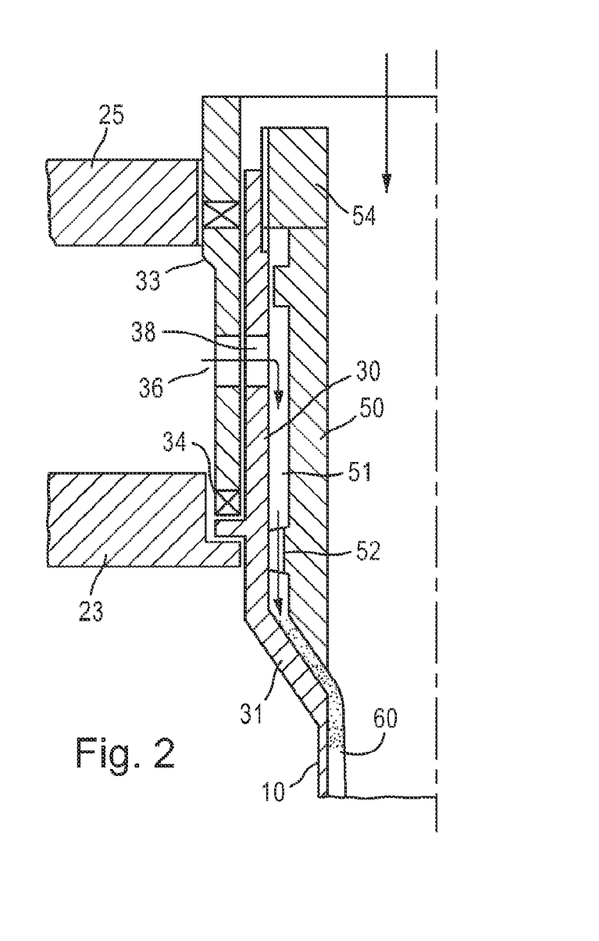
FIG. 2 is a diagram of the detail denoted by II in FIG. 1, on a larger scale.
Figure 3:
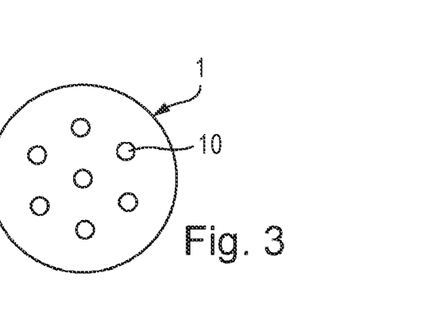
FIG. 3 is a diagram of the cross-section along line III-III in FIG. 1.

As shown in FIGS. 1-3, the reactor 1 contains a set of parallel tubes 10 enclosed in a cylindrical housing, which is connected at one end to a gaseous reagent feeding chamber 70 and at the other end to a product collection chamber 40.

Gaseous ozone from an external source, such as a corona discharge or electrolysis driven ozone generating device, flows through conduit 12 into the feeding chamber 70 where it enters the tubes 10 and reacts with the liquid or emulsified reagent.

Reaction product(s) emerge from the tubes 10 into the product collection chamber 40, from which the reaction product(s) are removed via conduit 13 and collected in an external vessel.

A liquid coolant, such as water and/or glycol, flows into the reactor housing through conduit 20, around the tubes 10 and out of the reactor housing via conduit 21. Alternatively, the liquid coolant flows into the reactor housing through conduit 21 and out via conduit 20. The in conduit 20 and out conduit 21 direction of flow for the liquid coolant is preferred, however, because the exothermic reaction between ozone and the liquid or emulsified reagent(s) takes place preferentially at the portion of the tubes 10 that is closest to the feeding chamber 70. Numerous diaphrams 22, located inside the reactor housing and oriented perpendicular to the tubes 10, increase alter the path and increase the turbulence of the coolant flowing through the reactor housing. The coolant is separated from the gas feeding chamber and the product collection chamber by plates 23 and 24, respectively, which are oriented normal to, and positioned at the ends of the tubes 10.

Additional configurations for cooling the reactor that are not depicted in FIGS. 1-3 are also effective and may be employed. For example, the reactor housing interior may contain two separate cooling sections, one to cool the end of the tubes 10 that is connected to the feeding chamber 70 and one too cool the end of the tubes 10 that is connected to the product collection chamber 40, to enhance the overall cooling capacity.

A third tube plate 25 is positioned between the gas feeding chamber 70 and plate 23 such to define a feeding chamber 15 for the liquid or emulsified reagent(s). One or more conduits 16 are used to feed the liquid or emulsified reagent(s) into the feeding chamber 15, which also contains a device as shown in FIG. 2 for introducing the liquid or emulsified reagent(s) into one end of the tubes 10.

As shown in FIG. 2, each tube 10 has a cylindrical portion 30 with a slightly larger diameter than the remainder of the tube, which is connected to the tube by a frusto-conical section 31. The cylindrical portion 30 contains passages 38 for introducing the liquid or emulsified reagent(s) into the tube 10. The cylindrical portion 30 fits, with suitable clearance, in a cylindrical sleeve 33, the latter of which facilitates for the formation of liquid-tight seals between the cylindrical portion 30 and plates 23 and 25. The cylindrical sleeve 33 contains passages 36 for the liquid or emulsified reagent(s), of suitable size and circumferential distribution as not to generate head losses when allowing passage of the liquid or emulsified reagent(s) into the cylindrical portion 30.

The outer surface of a second sleeve 50 is in contact with the inner surface of the cylindrical portion 30, except for a central section, owing to the presence of a wide annular groove 51. The inner surface of the cylindrical portion 30 and groove 51 define an annular space for receiving the liquid or emulsified reagent(s) that enter the tube 10 from the passages 36 and 38, which open into groove 51. A seal groove 34 is positioned between the cylindrical sleeve 33 and the frusto-conical section 31. Suitable axial passages 52, shown only diagrammatically in FIG. 2, allow the liquid reagent to discharge into the tube interior from the annular space defined by groove 51. The sleeve 50 comprises a beveled or frusto-conical end with the same opening angle as the frusto-conical section 31.

Between one end of the second sleeve 50 and the frusto-conical section 31 there is an annular slot oriented according to the generatrices of a truncated cone, the width of this slot being defined by the gap space between sleeve 50 and the frusto-conical section 31. The gap space between sleeve 50 and the frusto-conical section 31 may be adjusted by a threaded crown 54 screwed into the end of the cylindrical portion 30 that is closest to the gas feeding chamber 70. It is thus possible, by screwing up or down the sleeve 50 in the cylindrical portion 30, to adjust the cross-section of the annular slot between the edge of the sleeve 50 and the frusto-conical section 31. The annular slot, being orientated according to the generatrices of a cone, favors the distribution of the liquid reagent in the form of a film entirely around the inner surface of the tube 10.

The inner diameter of sleeve 50 is suitably the same as the inner diameter of the tube 10 so that the gaseous reagent coming from the distribution chamber 70 may be brought to brush the free surface of the film 60 without resulting in a significant head loss.

Starting materials for the method described herein include any compound that may be oxidized by ozonolysis. Specific examples of starting materials for this process include hydroxycitronellene, methoxycitronellene, fatty acid methyl esters (FAME), triglycerides, fatty acids, fatty alcohols, fatty esters, diterpenes, sesquiterpenes, monoterpenes, allyl ethers, alpha olefins, and rosin acids.

In one embodiment, a tube reactor for ozonolysis includes a tube (see, e.g., 10 in FIG. 1) with a 5 to 30 mm internal diameter (e.g., 10 mm) and a length of 1 to 7 m (e.g., 1.7 m). The tube is constructed of a suitable material (e.g., stainless steel) and is connected to a gaseous reagent feeding chamber (see, e.g., 70 in FIG. 1) that allows gas to flow through the center of the tube and liquid to be flowed in a film on the wall of the tube through annular slots (e.g., as shown in FIG. 2; component II in FIG. 1). The tube is enclosed in a jacket (see, e.g., 1 in FIG. 1) for circulating liquid coolant around it (see, e.g., 10 in FIG. 1), with the end of the tube protruding through a liquid-sealed orifice (see, e.g., 24 in FIG. 1). A liquid/gas separation vessel is connected to the bottom of the reaction tube (see, e.g., 10 in FIG. 1). The excess gas flows into an ice condenser and then into an ozone destruction unit. The collected liquid product is pumped into sampling containers for analysis by a peristaltic pump.

In one embodiment, the gas inlet (see, e.g., 12 in FIG. 1) is connected to an ozone generator, and the liquid inlet is connected to a stirred feed tank equipped with a peristaltic pump. The liquid inlet pipe is also jacketed and cooled to control the temperature of the feed liquid or emulsified reagent.

In one embodiment, for emulsion preparation, water is combined with the organic reagent in a ratio (e.g., 5:1) ranging from stoichiometric (i.e., 1:1) to very dilute (e.g., 100:1) in the feed tank and stirred vigorously such that a homogenous emulsion is maintained. Deionized water is used for the emulsions.

In one embodiment, a mixture of $O_2$ and $N_2$ gas is used to feed the ozone generator and to comprise the ozone carrier gas for the ozonolysis reaction.

In one embodiment, conversions of starting materials are determined by gas chromatography (GC) and are calculated on the basis of the disappearance of starting material. Samples are prepared by extracting the organic components of the emulsion into a homogenous organic solvent phase. Analysis of the composition of the aforementioned organic phase is accomplished by gas chromatography.

In one embodiment, the ratio of water to organic reagent ranges from 1:1 to 100:1 (e.g., 5:1), the ozone concentration ranges from 2.5% to 10% (e.g., 5%), the gas flow rate ranges from 10 to 20 L/min (e.g., 15 L/min), the ozone mass flow rate ranges from 32.6 to 135 g/h (e.g., 65.9 g/h), the emulsion flow rate ranges from 1 to 5 kg/h (e.g., 2 kg/h), and the cooling temperature ranges from 0 to 20° C. (e.g., 10° C.), to yield starting material conversion percentages ranging from 13.70% to 52.63% (e.g., 26.76%).

In another embodiment, 1-6 pilot tube reactors (e.g., 3) can be connected in series, with gas and liquid being separated at the bottom of each tube. Tubes can be from 1-6 m in length (e.g., 1.7 m), and the tubes can range in diameter from 5-50 mm (e.g., the first 2 tubes being 25 mm in diameter and the $3^{rd}$ tube being 10 mm in diameter). The organic liquid feed can be flowed in a solution of reagent and nonanoic acid in ranges from 1:1 to 100:1 (e.g., 3:1) through the first tube to the second and third tube in series at rates ranging from 1-99 kg/hr (e.g., 4.2 kg/hr). The gas can be flowed co-currently at ozone concentration in ranges from 0.5% to 10% (e.g., 5.1%) from the $3^{rd}$ tube through the $2^{nd}$ to the $1^{st}$ tube at a flow rate from 10 to 1500 L/min (e.g., 150 L/min), and the cooling jacket temperature can be maintained between 0 and 50° C. (e.g., 15° C.) to yield conversion percentages between 93-100% (e.g., 97.6%).

EXAMPLES

Example 1

Film Ozonolysis in a Monotubular Reactor
Ozonolysis Reactor Details

A pilot tube reactor was used for ozonolysis, including a tube with a 10 mm internal diameter and a length of 1.7 m (e.g., 10 in FIG. 1). The tube was constructed of 316 stainless steel and was connected to a gaseous reagent feeding chamber (e.g., 70 in FIG. 1) that allowed gas to be flowed through the center of the tube and liquid to be flowed in a film on the wall of the tube through annular slots (e.g., as shown in FIG. 2; component II in FIG. 1). The tube was enclosed in a steel jacket (e.g., 1 in FIG. 1) for circulating cooling fluid around the reaction tube (e.g., 10 in FIG. 1) with the end of the tube protruding through a liquid-sealed orifice (e.g., 24 in FIG. 1). A liquid/gas separation vessel was connected to the bottom of the reaction tube (e.g., 10 in FIG. 1). The excess gas flowed through to an ice condenser followed by an ozone destruction unit. The collected liquid product was pumped through a peristaltic pump to sampling containers for analysis.

The gas inlet (e.g., 12 in FIG. 1) was connected to an Ozonia Ozat CFS-2G ozone generator and the liquid inlet was connected to a stirred feed tank equipped with a peristaltic pump. The liquid inlet pipe was also jacketed and cooled to control the temperature of the feed liquid reagent.
Ozonolysis Reagent and Product Details Methoxycitronellene was >99% pure and was obtained from reaction of methanol with dihydromyrcene. Fatty acid methyl esters (FAME) was obtained from multiple sources including soy, palm, and algal oils and consisted of 72-89% methyl oleate as the primary component.

When methoxycitronellene is reacted, the major product is methoxymelonal. When FAME is reacted, the major products are methyl azelaldehyde and nonanal.

For the emulsion preparation, water was combined with the organic reagent in a 5:1 ratio in the feed tank and stirred vigorously such that a homogenous emulsion was maintained. Deionized water was used for all of the emulsions.

A mixture of 95% $O_2$ and 5% $N_2$ gas was used to feed the ozone generator and to comprise the carrier gas for $O_3$ to the reaction.

Conversions of starting materials were determined by GC (Agilent 6890N) and were calculated based on the disappearance of the starting material on a gross adjusted basis. Samples were prepared by extracting the organic components of the emulsion into a homogenous ethyl acetate solvent phase and analyzing the composition of said organic phase by gas chromatography.

Example reaction conditions and product distributions are outlined in Tables 1 and 2. Reactions were performed at various $O_3$ concentrations and mass flow rates.

TABLE 1

Methoxycitronellene in a water-based emulsion was oxidized by ozonolysis at different ozone concentrations and flow rates to yield the starting material conversion percentages shown.

| Sample | Ratio of Water to Organic Reagent | $O_3$ Conc (w/w) % | Gas Flowrate L/min | $O_3$ Mass Flow g/h | Emulsion Flow kg/h | Cooling Temp °C. | Conversion of Starting Material % |
|---|---|---|---|---|---|---|---|
| 1 | 5:1 | 2.5 | 15 | 32.6 | 2 | 10 | 13.70 |
| 2 | 5:1 | 2.5 | 15 | 32.6 | 2 | 10 | 15.79 |
| 3 | 5:1 | 5 | 15 | 65.9 | 2 | 10 | 26.76 |
| 4 | 5:1 | 5 | 15 | 65.9 | 2 | 10 | 24.71 |
| 5 | 5:1 | 10 | 15 | 135 | 2 | 10 | 48.89 |
| 6 | 5:1 | 10 | 15 | 135 | 2 | 10 | 52.63 |

TABLE 2

FAME (89% methyl oleate) in a water-based emulsion was oxidized by ozonolysis at different ozone concentrations and flow rates to yield the starting material conversion percentages shown.

| Sample | Ratio of Water to Organic Reagent | $O_3$ Conc. (w/w) % | Gas Flowrate L/min | $O_3$ Mass Flow g/h | Emulsion Flow kg/h | Cooling Temp °C. | Conversion of Starting Material % |
|---|---|---|---|---|---|---|---|
| 1 | 5:1 | 4 | 15 | 52.5 | 2 | 25 | 42.4 |
| 2 | 5:1 | 4 | 15 | 52.5 | 2 | 25 | 38.8 |
| 3 | 5:1 | 6.4 | 15 | 85 | 2 | 25 | 46.5 |
| 4 | 5:1 | 6.4 | 15 | 85 | 2 | 25 | 50.4 |
| 5 | 5:1 | 9.5 | 15 | 128 | 2 | 25 | 50.9 |
| 6 | 5:1 | 9.5 | 15 | 128 | 2 | 25 | 51.3 |

Example 2

Ozonolysis Reactor 2 Details

A second arrangement of involving 3 pilot tube reactors connected in series was used. All 3 tubes were 1.7 m in length, with the first 2 tubes being 25 mm in diameter and the $3^{rd}$ tube being 10 mm in diameter. All tubes were equipped with a film distribution head, a cooling jacket, and a gas liquid separator at the bottom. The organic, liquid feed was flowed from the first tube through the second and third tube in series. The gas was flowed co-currently from the $3^{rd}$ tube through the $2^{nd}$ to the $1^{st}$ tube. The cooling jacket temperature was maintained at 15° C.

In one instance, this reactor was used to process a 75% mixture of vegetable fatty acid in nonanoic acid. The major components of the vegetable fatty acid were estimated as follows: 77.65% oleic acid, 11.64% linoleic acid, 1.98% stearic acid, 4.4% palmitic acid, 2.9% myristic acid. The $O_3$ was generated using pure $O_2$ and a generator composed of 2 Pinnacle Quadblocks in a custom cabinet. The results of this run are presented in Table 3.

TABLE 3

Ozonolysis of vegetable fatty acid in a film ozonolysis reactor. Sample 1 was taken at 10 minutes, Sample 2 at 15 minutes, and Sample 3 at 20 minutes. Conversion was based on disappearance of starting material on GC FID as compared to an internal standard.

| Sample | Ratio of Vegetable Fatty Acid to Nonanoic Acid | $O_3$ Conc. (w/w) % | Gas Flowrate L/min | $O_3$ Mass Flow g/h | Liquid Flow kg/h | Cooling Temp °C. | Conversion of Starting Material (oleic/linoleic) % |
|---|---|---|---|---|---|---|---|
| 1 | 3:1 | 5.1 | 150 | 672 | 4.2 | 15 | 95.5/98.1 |
| 2 | 3:1 | 5.1 | 150 | 672 | 4.2 | 15 | 94.0/97.6 |
| 3 | 3:1 | 5.1 | 150 | 672 | 4.2 | 15 | 93.7/97.3 |

In another instance, this reactor was used to convert a 25% solution of dihydromyrcenol in water to hydroxymelonal. The results of this run are shown in Table 4.

TABLE 4

Ozonolysis of dihydromyrcenol, i.e., hydroxycitronellene, in the film ozonolysis reactor to generate hydroxymelonal. Samples were taken every 5 minutes. Conversion was based on GC FID results.

| Sample | Dihydromyrcenol to Water Ratio | $O_3$ % (w/w) | Gas flow (L/min) | $O_3$ Mass Flow (g/hr) | Liquid Flow (ml/min) | Cooling Temp (° C.) | Conversion of Starting Material (%) |
|---|---|---|---|---|---|---|---|
| 1 | 3:1 | 7.8 | 80 | 555.8 | 80 | 5-15 | 99.8 |
| 2 | 3:1 | 7.8 | 80 | 555.8 | 80 | 5-15 | 99.5 |
| 3 | 3:1 | 7.8 | 80 | 555.8 | 80 | 5-15 | 98.5 |
| 4 | 3:1 | 7.8 | 80 | 555.8 | 80 | 5-15 | 97.2 |
| 5 | 3:1 | 7.8 | 80 | 555.8 | 80 | 5-15 | 98.3 |

Similar results were obtained for the conversion of β-Ionone to generate cyclocitral.

INCORPORATION BY REFERENCE

The entire disclosure of each of the patent documents and scientific articles referred to herein is incorporated by reference for all purposes.

EQUIVALENTS

The disclosure can be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

What is claimed is:

1. A method of performing ozonolysis or ozone-based oxidation on a liquid or emulsified reagent using an industrial scale tubular falling film reactor with multiple tubes wherein the combined ozone and carrier gas flow is co-current, and wherein the ozonolysis occurs continuously without accumulation of large amounts of hazardous intermediates, and wherein the tubes are cooled by flow of a coolant;
wherein the liquid or emulsified reagent comprises a compound selected from hydroxycitronellene, methoxycitronellene, a rose ketone, fatty acid methyl esters, triglycerides, fatty alcohols, fatty esters, diterpenes, sesquiterpenes, monoterpenes, allyl ethers, alpha olefins, rosin acids, tertiary amines, alkenes, alkynes, amides, carboxylic acids, and aromatic compounds, provided that said compound is susceptible to ozone oxidation.

2. The method of claim 1, wherein method comprises two or more industrial scale tubular falling film reactors with multiple tubes connected in series to process a continuous stream of the liquid or emulsified reagent.

3. The method of claim 1, wherein the carrier gas is selected from air, oxygen ($O_2$), and an oxygen ($O_2$)/nitrogen ($N_2$) mixture.

4. The method of claim 3, wherein the carrier gas is air and the ozone concentration in the carrier gas is from 2.5% to 10%.

5. The method of claim 1, wherein the liquid or emulsified reagent is an emulsion in water.

6. The method of claim 1, wherein the reactor comprises the multiple tubes in parallel enclosed in a cylindrical reactor.

7. The method of claim 1, wherein the diameter of the tube(s) is between 5 mm and 30 mm.

8. The method of claim 7, wherein the diameter of the tube(s) is between 10 mm and 25 mm.

9. The method of claim 1, wherein the gas flow rate is from 10 to 1500 L/min in each of said tube or tubes.

10. The method of claim 1, wherein the gas flow rate is about 150 L/min in each of said tube or tubes.

11. The method of claim 1, wherein the tubes are between 1 and 7 meters in length or wherein the tubes are about 6 meters in length, or both.

12. A method of performing ozonolysis or ozone-based oxidation on a liquid or emulsified reagent using an industrial scale tubular falling film reactor with multiple tubes wherein the combined ozone and carrier gas flow is co-current, and wherein the ozonolysis occurs continuously without accumulation of large amounts of hazardous intermediates, and wherein the tubes are cooled by flow of a coolant, wherein the liquid or emulsified reagent comprises a fatty acid susceptible to ozone oxidation, wherein the carrier gas is air and the ozone concentration in the carrier gas is from 2.5% to 10%.

13. The method of claim 1, wherein the liquid or emulsified reagent comprises a compound selected from hydroxycitronellene, methoxycitronellene, fatty acid methyl esters, fatty alcohols, diterpenes, sesquiterpenes, and monoterpenes, provided that said compound is susceptible to ozone oxidation.

14. The method of claim 13, wherein the liquid or emulsified reagent comprises hydroxycitronellene.

15. The method of claim 13, wherein the liquid or emulsified reagent comprises methoxycitronellene.

16. The method of claim 13, wherein the liquid or emulsified reagent comprises a fatty acid methyl ester.

17. The method of claim 13, wherein the liquid or emulsified reagent comprises methyl oleate.

18. The method of claim 13, wherein the liquid or emulsified reagent comprises abietic acid or an ester thereof, pinene, limonene, ionone, or dihydromyrcenol.

19. The method of claim 1, wherein the product is selected from hydroxymelonal, methoxymelonal, methyl azealdehyde, nonanal, cyclocitral, or mixtures thereof.

20. The method of claim 1, wherein the product is hydroxymelonal.

21. The method of claim 1, wherein the product is methoxymelonal.

22. The method of claim 1, wherein the product is a mixture of methyl azealdehyde and nonanal.

23. The method of claim 4, wherein the carrier gas is air and the ozone concentration in the carrier gas is from 2.5% to 5%.

* * * * *